United States Patent
Nouri et al.

(10) Patent No.: US 6,660,382 B2
(45) Date of Patent: Dec. 9, 2003

(54) PROCESS FOR MANUFACTURING COATED GRANULES WITH MASKED TASTE AND IMMEDIATE RELEASE OF THE ACTIVE PRINCIPLE

(75) Inventors: Noureddine Nouri, Cannes (FR); Jean-Marc Zuccarelli, Antibes (FR); Charles Chauveau, Valbonne (FR); Etienne Bruna, Jouy (FR)

(73) Assignee: Ethypharm, Houdan (FR)

( * ) Notice: Subject to any disclaimer, the term of this patent is extended or adjusted under 35 U.S.C. 154(b) by 0 days.

(21) Appl. No.: 10/041,389

(22) Filed: Jan. 8, 2002

(65) Prior Publication Data
US 2002/0098227 A1 Jul. 25, 2002

Related U.S. Application Data

(63) Continuation of application No. PCT/FR00/01855, filed on Jun. 30, 2000.

(30) Foreign Application Priority Data
Jul. 8, 1999 (FR) .............................. 99 09047

(51) Int. Cl.$^7$ ................................. B32B 5/16
(52) U.S. Cl. .................. 428/403; 428/407; 427/212; 427/213.3; 427/213.31; 427/213.36; 424/465; 424/480; 424/482; 424/499; 514/772.2; 514/781
(58) Field of Search .................. 428/403, 407; 424/465, 499, 480, 482; 514/772.2, 781; 427/212, 213.36, 213.31, 213.3

(56) References Cited

U.S. PATENT DOCUMENTS

| | | | |
|---|---|---|---|
| 4,726,966 A | | 2/1988 | Kawashima et al. ... 427/213.36 |
| 4,897,270 A | * | 1/1990 | Deutsch et al. ............. 424/465 |
| 5,149,542 A | * | 9/1992 | Valducci ..................... 424/493 |
| 5,288,501 A | * | 2/1994 | Nurnberg |
| 5,358,717 A | | 10/1994 | Kuramoto et al. .......... 424/464 |
| 5,380,535 A | * | 1/1995 | Geyer et al. ................ 424/484 |
| 6,194,000 B1 | * | 2/2001 | Smith et al. ................ 424/458 |
| 6,451,345 B1 | * | 9/2002 | Percel et al. ................ 424/480 |
| 6,475,510 B1 | * | 11/2002 | Venkatesh et al. .......... 424/441 |

FOREIGN PATENT DOCUMENTS

| | | |
|---|---|---|
| EP | 0 237 506 | 9/1987 |
| EP | 0 255 725 | 2/1988 |
| FR | 2785539 | 5/2000 |
| WO | WO98/47493 | 10/1998 |
| WO | WO99/09958 | 3/1999 |

OTHER PUBLICATIONS

Note for Guidance on Modified Release Oral and Transdermal Dosage Forms: Section II (Quality) *The European Agency for the Evaluation of Medicinal Products,* Human Medicines Evaluation Unit, London, 1–14, (Apr. 22, 1998).

* cited by examiner

*Primary Examiner*—Leszek Kiliman
(74) *Attorney, Agent, or Firm*—Heslin Rothenberg Farley & Mesiti P.C.

(57) ABSTRACT

The invention concerns a method for making coated granules with masked taste and instant release of the active principle which consists in: first, mixing the constituents of a powder comprising at least the active principle and a granular disintegrating agent; then, granulating the resulting powder, in the presence of a mixture of carriers comprising at least a binding agent capable of binding the particles together to obtain grains; coating the grains formed by spraying a suspension comprising at least a coating agent and a membrane disintegrating agent; finally drying the resulting coated granules.

25 Claims, 2 Drawing Sheets

PROCESS FOR MANUFACTURING COATED GRANULES WITH MASKED TASTE AND IMMEDIATE RELEASE OF THE ACTIVE PRINCIPLE

CROSS REFERENCE TO RELATED APPLICATIONS

This application is a continuation of PCT application PCT/FR00/01855 filed Jun. 30, 2000, and published under PCT Article 21(2) in French as WO 01/03672 on Jan. 18, 2001. PCT/FR00/01855 claimed the priority of French application FR/99 09047, filed Jul. 8, 1999. The entire disclosures of both are incorporated herein by reference.

The invention relates to a process for manufacturing coated granules with masked taste and immediate release of active principle. The invention also relates to the granules coated with active principle which may be obtained by this process, and also to any presentation form incorporating said coated granules.

In the description hereinbelow and in the claims, the expression "immediate release of active principle" means that the release kinetics of the active molecule are not substantially modified by the formulation and/or by the parameters of the manufacturing process (see in particular the document from the European Drug Agency "note for guidance on modified release oral and transdermal dosage forms" dated Apr. 22, 1998). Consequently, the dissolution profile of the active principle depends essentially on its intrinsic properties.

To obtain an immediate release of the active principle, document EP-A-0 237 506 proposes a complex process for manufacturing a fast-disintegrating granule, in which a solution of an active principle in a mixture of water and alkanol is first prepared and an emulsifier is then added thereto, the mixture obtained being vigorously homogenized. The composition thus obtained is sprayed onto a bed of powder comprising an inert support consisting of a microcrystalline cellulose and a disintegrant. The resulting aggregate is finally dried and then presented in more or less spherical form. The main object of this process is not to produce granules of active principle with masked taste.

Specifically, it is well known that a certain number of active principles have an unpleasant taste, such that it is essential to mask the taste of these active principles at least while they are in the oral cavity, so as to make them more pleasant to take and to optimize the patient's compliance with the treatment.

One of the solutions proposed consists in coating the particles of active principle with a cellulose polymer. However, although the taste of the active principle present in the granules is satisfactorily masked, the low permeability and low solubility of all the pH values of the cellulose polymer leads to a slow release of the active principle, which is unsuitable for immediate-release kinetics.

To solve this problem, the Applicant has proposed, in French patent application FR 98/14033 which is unpublished at the date of filing of the present application, to coat ibuprofen particles by spraying with a solution based on ethylcellulose and hydroxypropylmethylcellulose, also comprising an agent for promoting the dissolution of the ibuprofen.

Another solution consists in coating the particle of active principle with a polymer of the acrylic type. Among these polymers that may be distinguished are pH-dependent polymers, that is to say polymers whose solubility depends on the pH, and pH-independent polymers, that is to say polymers whose solubility is independent of the pH.

Depending on their solubility range, pH-dependent polymers may bring about a delayed release of the active principle just until it is into the distal portion of the intestine. In other words, such a coating is incompatible with an immediate release of the active principle.

pH-independent acrylic polymers are, by definition, insoluble, such that even though they are entirely satisfactory in terms of masking the taste, they too are unsuitable, on the basis of their permeability properties, for an immediate release of the active principle.

The use of this type of polymer is more particularly described in documents U.S. Pat. No. 4,726,966 and WO 98/47493.

Document U.S. Pat. No. 4,726,966 describes a process for manufacturing ibuprofen microspheres by dissolving ibuprofen particles in an aliphatic alcohol, followed by recrystallization in the form of microspheres with the aid of various solvents and acrylic resins. This manufacturing process, performed by means of a very specific technique, makes it possible to obtain a masking of the taste that is, in principle, satisfactory.

Similarly, document Wo 98/47493 describes a pharmaceutical composition in the form of granules coated with a polymer film of the acrylic type, which, as expressly indicated, leads to a delayed release of the active principle.

Similarly, document EP-A-0 255 725 describes the use of formulation adjuvants (binders and disintegrants) in the outer layer of sustained-release granules, presented in the form of tablets. In this case, the formulation adjuvants, including crosslinked sodium croscarmellose and povidone derivatives, are used to give the sustained-release granules sufficient cohesion during the tabletting procedure while at the same time ensuring rapid disintegration of the tablet.

Document EP-A-0 525 389 describes a process for producing multiparticulate tablets with rapid disintegration, which is imparted by using granules of active principle coated in particular with crospovidone. This compound is introduced here with the aim of giving the tablet rapid disintegration while at the same time maintaining sufficient cohesion.

However, for both these documents, the rapid disintegration of the tablet does not automatically mean immediate release of active principle.

In other words, the object of the invention is to propose a process for manufacturing coated granules, the taste of the active principle of which is masked, and the release of the active principle of which is immediate, irrespective of the nature of the coating polymer.

To do this, the invention proposes a process for manufacturing coated granules with masked taste, and immediate release of the active principle, according to which:

the constituents of a powder comprising at least the active principle and a granular disintegrant are first dry-mixed;

the powder obtained is then granulated, in the presence of a mixture of excipients comprising at least one binder capable of binding the particles together to give grains;

the grains thus formed are then coated by spraying with a suspension comprising at least one coating agent and a membrane disintegrant;

finally, the coated granules obtained are dried.

In the description hereinbelow and in the claims, the expression "membrane disintegrant" denotes an excipient that is capable of increasing the speed of disintegration of the coating layer of the granules, obtained after the coating step.

Similarly, the expression "granule disintegrant" denotes an excipient capable of accelerating the speed of separation of the particles of active principle from each other after dissolving the coating layer of the granule.

"Superdisintegrants", also known as high-performance disintegrants, are used as external disintegrant (AGM) and internal disintegrant (AGG). Superdisintegrants are widely known to those skilled in the art, and are more particularly described in the publication Journal of Pharmaceutical Sciences (Volume 85, No. 11, November 1996).

In the process of the invention, the granular and membrane disintegrants are advantageously chosen from the group comprising sodium carboxymethylcellulose, crospovidone and carboxymethylstarch.

The process of the invention makes it possible, surprisingly and unexpectedly, to solve the two problems with diametrically opposed solutions, namely those of achieving the masking of the taste of the active principle by coating, while not, however, delaying the dissolution of the active principle, and in doing so by incorporating both at the granular level and at the membrane level, not only a binder and a coating agent, respectively, but also (granular and membrane) disintegrants.

The distinction between the actual granulation and coating steps is relatively theoretical, insofar as, even though the primary function of the binder used in the granulation step is to bind together the particles of active principle and the AGG, it nevertheless already partially coats the grains formed.

Similarly, even though the essential function of the coating agent used in the actual coating step is to complete the final coating of each of the grains, it may, however, arbitrarily bind other coated grains by a mechanism of granular agglomeration.

In a first embodiment of the process of the invention, the binder and the coating agent are chosen from the group comprising cellulose polymers and acrylic polymers.

However, even though the binder and the coating agent are chosen from the same group of compounds, they nevertheless differ from each other in their function as previously mentioned.

Among the cellulose polymers that will be advantageously chosen are ethylcellulose, hydroxypropylcellulose (HPC), carboxymethylcellulose (CMC) and hydroxypropylmethylcellulose (HPMC), alone or as a mixture.

Among the acrylic polymers that will be advantageously chosen are the ammonio-methacrylate copolymer (Eudragit® RL or RS), the polyacrylate (Eudragit® NE) and the methacrylic acid copolymer (Eudragit® L or S), Eudragit® being a registered trademark of Rohm.

In one advantageous embodiment, the binder is of the same nature as the coating agent.

To further accelerate the release of the active principle, the coating suspension also comprises a permeabilizer which, on account of its intrinsic solubility properties, causes perforation of the membrane coating, thus allowing the active principle to be released.

Among the permeabilizers that may be used, povidone and its derivatives, polyethylene glycol, silica, polyols and low-viscosity cellulose polymers are distinguished.

Polymers of the type such as hypromellose, whose viscosity is equal to 6 centipoises, are used, for example, as low-viscosity cellulose polymer.

In order to allow a similar action at the granular level to be obtained, that is to say to promote the release of the bound particles of active principle at the level of the grains formed after the granulation step, the excipient mixture used in the granulation step also comprises a permeabilizer of the type described above.

Moreover, to optimize the masking of the taste of the active principle, the suspension sprayed during the coating step also comprises a sweetener.

Similarly, to obtain masking of the taste of the active principle throughout the process of disintegration of the coated granule, that is to say not only as regards the gradual disintegration of the film for coating the granule, but also as regards the subsequent separation of the particles of active principle, the dry mix of initial powder may also comprise a sweetener.

Sweeteners which may be used include aspartam, potassium acesulfam, sodium saccharinate, neohesperidine dihydrochalcone, monoammonium glycyrrhizinate, sugars and derivatives, and also polyols and derivatives, alone or as a mixture.

Furthermore, to give the coating suspension and the dry mix of initial powder antistatic properties, they comprise an antistatic agent chosen from the group comprising precipitated or colloidal silica, and talc.

Needless to say, the granulation and coating steps may be performed in different devices or in the same device and in the presence, for each step, of a mixture of excipients of identical or different nature.

In a first embodiment, the dry-mixing of initial powder and the granulation, coating and drying steps are performed in a fluidized bed.

In this case, the initial powder mixture is first fluidized before being granulated by spraying said powder with the excipient mixture comprising at least the binder, the grains obtained then being coated by spraying with the coating suspension, the coated granules formed finally being dried in the fluidized bed.

In one advantageous embodiment, the mixture of excipients used during the granulation step and the coating suspension used during the coating step form a single mixture. In this case, the granulation step will be distinguished from the spraying step by varying different parameters, such as the rate of spraying of the mixture and the atomization pressure of said mixture. Thus, only some of the mixture of excipients will be used during the granulation step, while the other portion will be used during the coating step.

Thus, the rate of spraying of the coating suspension is higher during the granulation step than during the coating step, whereas the atomization pressure of the coating suspension is lower during the granulation step than during the coating step.

In practice, at the laboratory scale in a fluidized-bed device, for example of the type such as Glatt GPCG1, during the granulation step, the rate of spraying of the coating suspension is between 10 and 25 grams/minute, and the atomization pressure is between 1 and 1.8 bar.

During the coating step, the rate of spraying of the coating suspension is between 5 and 15 grams/minute, while the atomization pressure is between 1.5 and 2.5 bar.

In one preferred embodiment, between 10 and 20% of the mixture of excipients is sprayed during the granulation step, the remainder to 100% being sprayed during the coating step.

In other words, and according to this advantageous process, after the active principle, the granular disintegrant and advantageously a sweetener have been dry-mixed, the fluidized bed is sprayed with a suspension of excipients comprising the membrane disintegrant, the coating agent, the binder and the permeabilizer, by varying the rate of spraying and the atomization pressure of said suspension, so as to obtain first granulation and then coating of the grains formed.

However, in another embodiment, still in the same device, the first mixture of excipients is of a different nature from the second, and in particular contains no membrane disintegrant.

In another embodiment, the granulation step and the coating step are carried out in different devices.

Thus, it will be possible, for example, to carry out the granulation step in a paddle granulator or in a plowshare granulator, while the coating step may be carried out in a fluidized bed. Needless to say, as previously, the mixture of excipients used during the granulation step and during the coating step may be identical or different.

The invention also relates to the coated granules which may be obtained by the process described above.

In one advantageous embodiment, the coated granules of the invention comprise, by weight of the coated granule:
   from 5 to 70% of a coating polymer,
   from 0.5 to 15% of a granule disintegrant,
   from 1 to 20% of a membrane disintegrant,
   from 1 to 20% of a permeabilizer.

For a coating polymer concentration of less than 5%, the coating is insufficient to permit good masking of the taste. For a concentration of greater than 70%, the release of the active principle is retarded.

Similarly, for an amount of granular and membrane disintegrants of less than 1%, the release is not immediate. Similarly, for a concentration of greater than 20%, the masking of the taste is insufficient.

In parallel, for a permeabilizer concentration of less than 1%, the release is retarded, while for a concentration of greater than 20%, the masking of the taste is insufficient.

In order to be able to optimize the masking of the taste, the granules also comprise between 1 and 20% of sweetener.

Needless to say, the coating polymer, disintegrants, permeabilizer and sweetener are chosen from the compounds described above.

In one advantageous embodiment, the coated granules of the invention comprise, by weight of the coated granule:
   from 10 to 40% ethylcellulose,
   from 3 to 10% crospovidone,
   from 2 to 10% polyethylene glycol,
   from 2 to 10% aspartam.

Needless to say, the coated granules manufactured according to the process of the invention may be used, depending on the choice of the main polymer and the properties imparted to the coating, in any suitable presentation formulation.

Among these formulations that will advantageously be chosen are tablets of the fast-crumbling multiparticulate tablet type as described by the applicant in document FR-A-2 679 451, complying with the orodispersible tablet monograph of the European Pharmacopea.

However, the coated granules of the invention may also be used in "fast-dispersible" tablets, that is to say in tablets that disperse quickly in water, capable of breaking down in a very short period, of less than 1 minute and preferably less than 15 seconds, in a minimum volume of water, which will depend on the mass of the tablet.

Finally, the coated granules may be used in standard presentation formulations of the type such as a sachet, suspension, etc.

The invention and the advantages resulting therefrom will emerge more clearly from the following implementation examples in support of the attached figures, in which.

Figure 1:
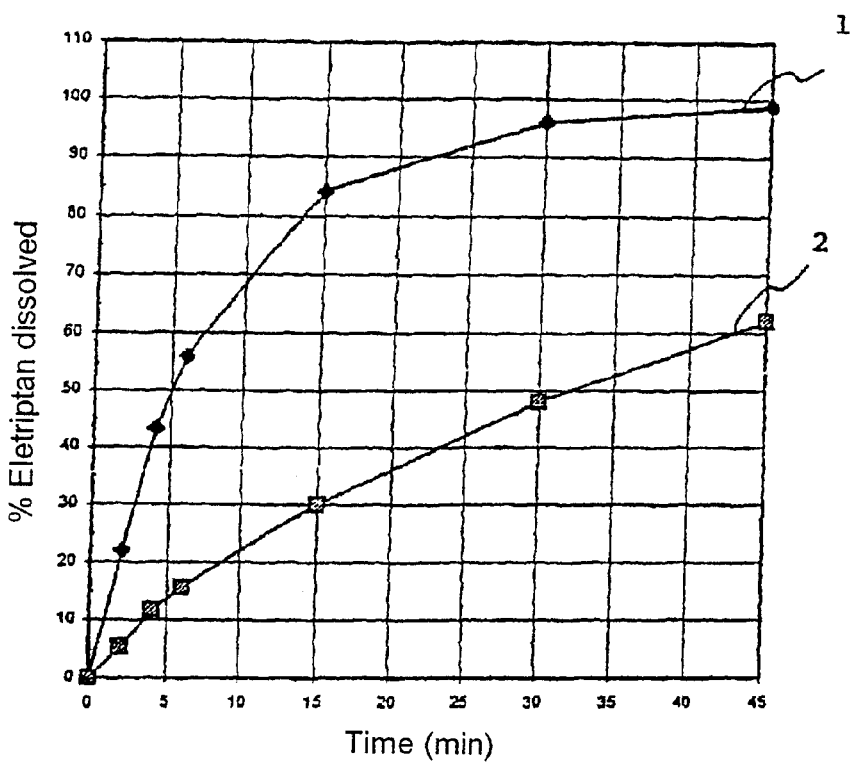
FIG. 1 is a representation of the dissolution profile of a fast-crumbling multiparticulate eletriptan tablet manufactured from granules coated with or without granular and membrane disintegrant (AGG and AGM)

The granulation and coating steps carried out in each of the three examples below are performed in a fluidized bed in the same device sold by the company Glatt under the name Glatt GPCG1.

Moreover, and for each of the examples below, taste-masking tests were performed on a sample of individuals. The results are indicated as a function of the following scale:
   active principle taste undetected
   active principle taste detected slightly
   active principle taste present
   active principle taste at the limit of acceptability
   active principle taste unacceptable

EXAMPLE 1

Eletriptan-based Coated Granule Incorporated Into a Tablet of the Fast-crumbling Multiparticulate Type As already stated, fast-crumbling multiparticulate tablets are known and described more particularly in document FR-A-2 679 451 by the applicant.

To manufacture these tablets, the process begins by preparing coated granules of active principle, the composition of which is as follows:

| COATED GRANULE COMPOSITION | | |
|---|---|---|
| Active principle | Eletriptan (salt) | 98.5 mg (equivalent to 80 g of base active principle) |
| AGG | Sodium croscarmellose[1] | 4.90 mg |
| Coating agent | Ethylcellulose | 20.40 mg |
| Permeabilizer | Polyoxyethylene glycol 6000 | 4 mg |
| AGM | Sodium croscarmellose | 3.70 mg |
| Flow/antistatic agent | Precipitated silica | 1.40 mg |
| Sweetener | Aspartam | 3.90 mg |

[1]Acdisol sold by FMC

The granules are manufactured according to the following process. A granulation solution is first prepared by dissolving 48 g of ethylcellulose in 273 g of ethyl alcohol.

A coating suspension is then prepared by mixing 97 g of ethylcellulose, 28.5 g of polyethylene glycol 6000, 26 g of sodium croscarmellose, 10 g of precipitated silica and 27.5 g of aspartam in 1900 g of ethyl alcohol, until a homogeneous suspension is obtained.

The powder mixture consisting of 700 grams of eletriptan and 35 grams of Acdisol is then fluidized.

The granulation is then started by spraying the granulation solution for about 15 to 20 minutes at a spraying rate of 25 grams/minute and a suspension atomization pressure of 0.8 bar.

The actual coating is then performed, by spraying the coating suspension for about 1 hour 30 minutes at a spraying rate of about 15 to 20 grams/minute and a suspension spraying pressure of 1.5 bar.

The coated granules thus obtained are then formulated as fast-crumbling multiparticulate tablets, the composition of which is as follows:

| TABLET COMPOSITION | | |
|---|---|---|
| Coated granules | Eletriptan (salt) | 136.8 mg (equivalent to 80 g of base active principle) |
| Tabletting agent | Mannitol | 575.20 mg |
| Tablet disintegrant | Sodium croscarmellose | 24 mg |
| Sweetener | Aspartam | 30 mg |
| Flavoring | Mint liquorice flavoring | 10 mg |
| Lubricant | Magnesium stearate | 8 mg |

The tablets are manufactured by screening all the excipients, followed by homogenization of the granules coated with the mixture of excipients in a plowshare granulator. The granules obtained are then distributed and shaped on a rotary tabletting machine. The hardness of the tablets obtained is about 30 N.

Result

Taste Masking

The tasting tests performed on the tablets are satisfactory: active principle taste not detected.

Release Profile of the Eletriptan

Dissolution kinetics of the eletriptan tablets manufactured are performed in a device of the type I, according to the European Pharmacopea 3rd edition, in 0.1 N HCl acid medium, with a dissolution volume of 900 ml. The number of paddle turns per minute is equal to 100.

FIG. 1 shows the dissolution profile of eletriptan tablets with disintegrants (AGG and AGM) (curve 1) and without a disintegrant (curve 2). As this figure shows, the presence of disintegrants introduced not only into the granulation (AGG) but also into the granule coating step (AGM) produces an immediate release of the active principle.

EXAMPLE 2

Ibuprofen-based Coated Granule Incorporated into a Tablet of the Fast-crumbling Multiparticulate Type Ibuprofen granules are prepared, the composition of which is as follows:

| GRANULE COMPOSITION | | |
|---|---|---|
| Active principle | Ibuprofen | 200 mg |
| Granule disintegrant (AGG) | Sodium croscarmellose | 16 mg |
| Sweetener | Aspartam | 27.5 mg |
| Flow/antistatic agent | Precipitated silica | 12.20 mg |
| Coating agent | Ethylcellulose | 35 mg |
| Permeabilizer | Hypromellose[1] | 8 mg |
| Membrane disintegrant (AGM) | Sodium croscarmellose | 1.33 mg |

[1]Pharmacoat 606 sold by Shin Etsu

In this example, the excipient mixture used during the granulation step and the coating suspension used during the coating step form the same mixture.

Said mixture is a suspension obtained by mixing ethylcellulose, the membrane disintegrant, 80% precipitated silica and 30% aspartam in ethyl alcohol, until a homogeneous suspension is obtained.

The powder mixture consisting of ibuprofen, the granule disintegrant, 70% aspartam and 20% precipitated silica is then fluidized.

The granulation is then started by spraying the mixture for about 15 to 20 minutes at a spraying rate of 25 grams per minute and a suspension atomization pressure of 0.8 bar.

The actual coating is then performed by spraying the remainder of the mixture over about 1 hour 30 minutes at a spraying rate of 15 to 20 grams per minute and a suspension atomization pressure of 1.5 bar.

15% of the mixture is sprayed during the granulation step, the remainder to 100% being sprayed during the coating step.

The granules obtained are then formulated as fast-crumbling multiparticulate tablets, the composition of which is as follows:

| TABLET COMPOSITION | | |
|---|---|---|
| Coated granules | | 300 mg |
| Diluent | Mannitol | 344 mg |
| Tablet disintegrant | Sodium croscarmellose | 21 mg |
| Flow agent | Precipitated silica | 7 mg |
| Sweetener | Aspartam | 20 mg |
| Flavoring | Mint flavoring | 4 mg |
| Lubricant | Magnesium stearate | 4 mg |

Results

Taste Masking

The masking of the taste is satisfactory: active principle taste not detected.

Release Profile

The dissolution kinetics are performed in a device of type II according to the European Pharmacopea 3rd edition.

Figure 2:
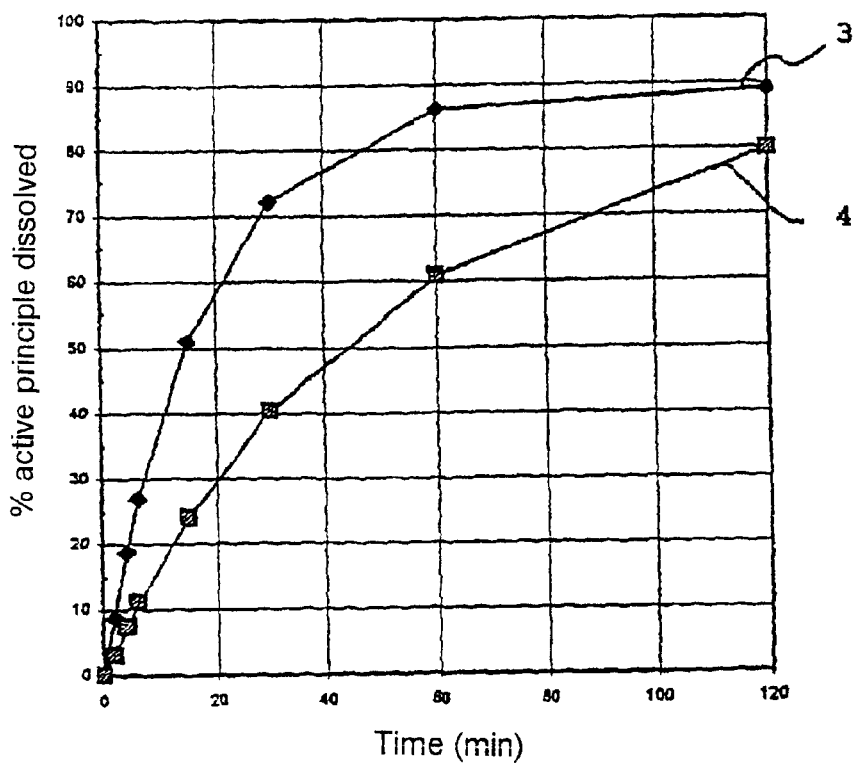
FIG. 2 is a representation of the dissolution profile of a fast-crumbling multiparticulate ibuprofen tablet manufactured from granules coated with or without disintegrant (AGG and AGM)

FIG. 2 shows the dissolution profile of ibuprofen tablets with or without disintegrant (curves 3 and 4, respectively).

EXAMPLE 3

Pregabaline-based Coated Granule Incorporated into a Tablet of Fast-crumbling Multiparticulate Type Pregabaline granules are prepared, the composition of which is as follows:

| GRANULE COMPOSITION | | |
|---|---|---|
| Active principle | Pregabaline | 150 mg |
| AGG | Crospovidone[1] | 6.43 mg |
| Sweetener | Potassium acesulfam[2] | 7.5 mg |
| Flow/antistatic agent | Precipitated silica | 4.28 mg |
| Coating agent | Ethylcellulose | 39.64 mg |
| AGM | Crospovidone | 6.43 mg |

[1]Kollidon CL sold by BASF
[2]Sunett sold by Nutrinova

The process for manufacturing the coated granules is similar to that of Example 2, the only difference being that the active principle, the AGG, half of the mass of sweetener and half of the mass of antistatic agent are dry-mixed.

The granules obtained are then formulated as fast-crumbling multiparticulate tablets, the composition of which is as follows:

| GRANULE COMPOSITION | | |
|---|---|---|
| Coated granules | | 150 mg |
| Tabletting agent | Mannitol | 474 mg |
| Disintegrant | Cropovidone[1] | 80 mg |
| Sweetener | Aspartam | 14 mg |
| Flavoring | Flavoring | 8 mg |
| Lubricant | Magnesium stearate | 8 mg |

[1]Kollidon CL sold by BASF

The multiparticulate tablets are manufactured according to a process that is identical to that of example 1.
Results
Taste Masking
The tasting tests performed on the tablets are satisfactory.
Pregabaline Release Profile
The dissolution kinetics are performed in a device of type II according to the European Pharmacopea 3rd edition.

Dissolution kinetics are performed on the tablets obtained in a device of type II in 0.06 N HCl medium, with a dissolution volume of 900 ml, and with a paddle speed of 50 rpm.

Figure 3:
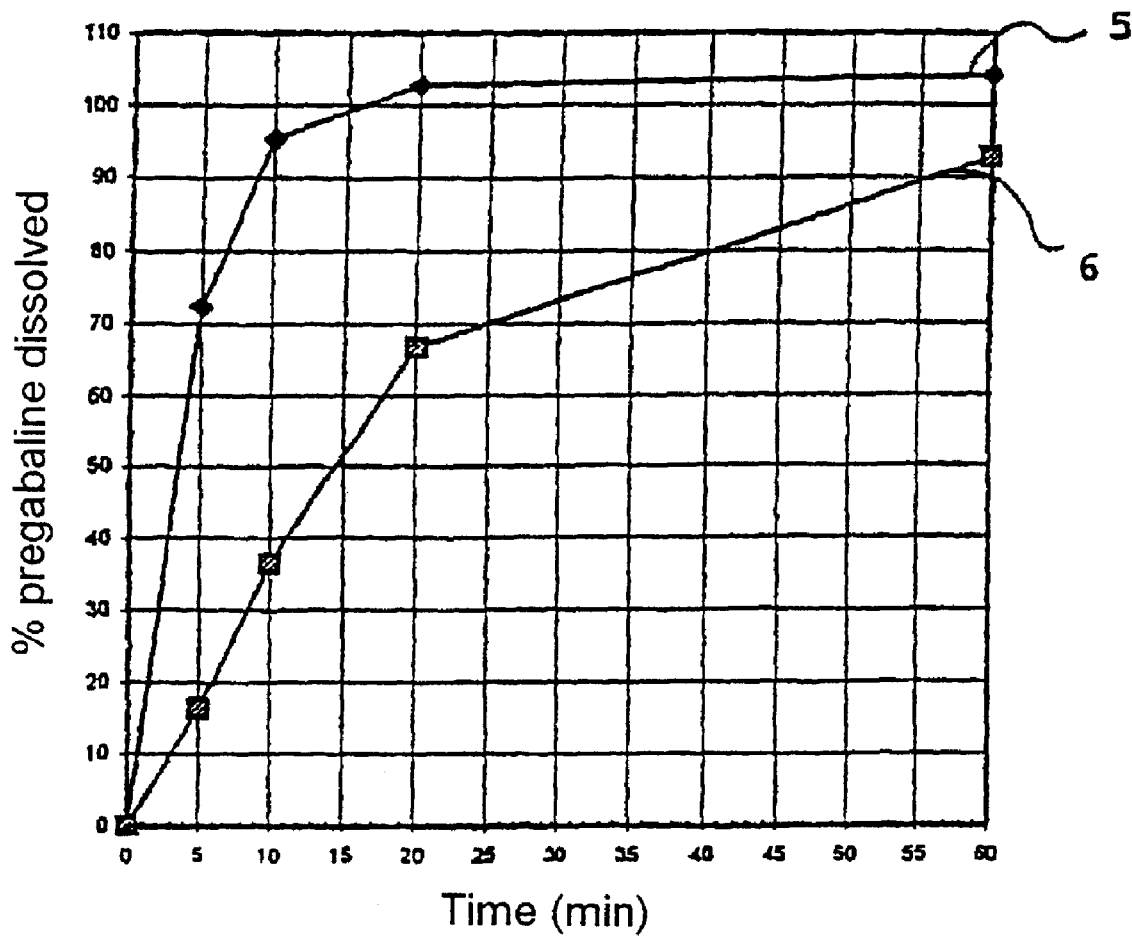
FIG. 3 is a representation of the dissolution profile of a fast-crumbling multiparticulate pregabaline tablet manufactured from granules coated with or without disintegrant (AGG and AGM).

FIG. 3 shows the dissolution profile of pregabaline tablets comprising a disintegrant (curve 5) and that of pregabaline tablets without a disintegrant (curve 6).

Curve 5 shows that the pregabaline is released immediately.

The advantages of the invention emerge clearly from the description.

It will be noted in particular that it is possible to obtain a formulation in which the taste of the active principle is masked, without, however, delaying the release of the active principle.

Moreover, the characteristic granulation and coating step of the process of the invention may be carried out in different devices or in the same device, and with a choice of identical or different mixtures of excipients.

In addition, the coated granules obtained may be incorporated into any suitable presentation form of the type such as a gel capsule, a multiparticulate tablet, a tablet, a sachet, etc.

What is claimed is:

1. A process for manufacturing coated granules with masked taste, and immediate release of the active principle, according to which:

the constituents of a powder comprising at least the active principle and a granular disintegrant are first dry-mixed;

the powder obtained is then granulated, in the presence of a mixture of excipients comprising at least one binder for binding the particles together to give grains;

the grains formed are then coated by spraying with a suspension comprising at least one coating agent and a membrane disintegrant;

finally, the coated granules obtained are dried.

2. A process for manufacturing coated granules with masked taste, and immediate release of the active principle, according to which:

the constituents of a powder comprising at least the active principle and a granular disintegrant are first dry-mixed;

the powder obtained is then granulated, and the grains formed are then coated, in the presence of the same mixture of excipients comprising at least one binder for binding particles together to give grains; at least one coating agent and a membrane disintegrant; the rate of spraying of the mixture of excipients being higher during the granulation step than during the coating step, and the atomization pressure of the mixture of excipients being lower during the granulation step than during the coating step;

finally, the coated granules obtained are dried.

3. The manufacturing process as claimed in claim 2, characterized in that between 10 and 20% of the mixture of excipients is sprayed during the granulation step, the remainder being sprayed during the coating step.

4. The process for manufacturing coated granules as claimed in claim 1, characterized in that the granule and membrane disintegrants are high-performance disintegrants chosen from the group consisting of sodium carboxymethylcellulose, crospovidone and carboxymethyl-starch.

5. The process for manufacturing coated granules as claimed in claim 1, characterized in that the binder and the coating agent are chosen from the group consisting of cellulose polymers and acrylic polymers.

6. The process for manufacturing coated granules as claimed in claim 5, characterized in that the cellulose polymer is chosen from the group consisting of ethylcellulose, hydroxypropylcellulose (HPC), carboxymethylcellulose (CMC), hydroxypropylmethylcellulose (HPMC), and combinations thereof.

7. The process for manufacturing coated granules as claimed in claim 5, characterized in that the acrylic polymer is chosen from the group consisting of acrylic polymers and methacrylic polymers, ammonio-methacrylate copolymer, polyacrylate and methacrylic acid copolymer.

8. The process for manufacturing coated granules as claimed in claim 1, characterized in that the suspension also comprises a permeabilizer.

9. The process for manufacturing coated granules as claimed in claim 1, characterized in that the mixture of excipients used in the granulation step also comprises a permeabilizer.

10. The manufacturing process as claimed in claim 2, characterized in that the mixture of excipients also comprises a permeabilizer.

11. The process for manufacturing coated granules as claimed in claim 8, wherein the permeabilizer is chosen from the group consisting of cellulose polymers having a viscosity of 6 centipoises or less, povidone, povidone derivatives, polyethylene glycol, silica, and polyols.

12. The process for manufacturing coated granules as claimed in claim 1, characterized in that the suspension sprayed during the coating step also comprises a sweetener.

13. The process for manufacturing coated granules as claimed in claim 1, characterized in that the dry mix of initial powder also comprises a sweetener.

14. The manufacturing process as claimed in claim 2, characterized in that the mixture of excipients also comprises a sweetener.

15. The process for manufacturing coated granules as claimed in claim 12, wherein the sweetener is chosen from the group consisting of aspartame, potassium acesulfame, sodium saccharinate, neohesperidine dihydrochalcone, monoammonium glycyrrhizinate, a sugar, a sugar derivative, a polyol, a polyol derivative and combinations thereof.

16. The process for manufacturing coated granules as claimed in claim 1, characterized in that the dry-mixing of initial powder, the granulation, the coating and the drying are performed in a fluidized bed.

17. A coated granule obtained by the process of claim 1.

18. The coated granule as claimed in claim 17, characterized in that it comprises, by weight of the coated granule:

from 5 to 70% of a coating polymer, from 0.5 to 15% of a granule disintegrant, from 1 to 20% of a membrane disintegrant, from 1 to 20% of a permeabilizer.

19. The coated granule as claimed in claim 18, characterized in that it also comprises from 1 to 20% by weight of a sweetener.

20. The coated granule as claimed in claim 19, characterized in that it comprises, by weight of the coated granule:

from 10 to 40% ethylcellulose, from 3 to 10% crospovidone, from 2 to 10% polyethylene glycol, from 2 to 10% aspartam.

21. A fast-crumbling multiparticulate tablet comprising the granules of claim 17.

22. A fast-dispersible tablet comprising the granules of claim 17.

23. The process for manufacturing coated granules as claimed in claim 9, wherein the permeabilizer is chosen from the group consisting of cellulose polymers having a viscosity of 6 centipoises or less, povidone, povidone derivatives, polyethylene glycol, silica, and polyols.

24. The process for manufacturing coated granules as claimed in claim 13, wherein the sweetener is chosen from the group consisting of aspartame, potassium acesulfame, sodium saccharinate, neohesperidine dihydrochalcone, monoammonium glycyrrhizinate, a sugar, a sugar derivative, a polyol, a polyol derivative and combinations thereof.

25. The process for manufacturing coated granules as claimed in claim 14, wherein the sweetener is chosen from the group consisting of aspartame, potassium acesulfame, sodium saccharinate, neohesperidine dihydrochalcone, monoammonium glycyrrhizinate, a sugar, a sugar derivative, a polyol, a polyol derivative and combinations thereof.

* * * * *